United States Patent
Covella et al.

(10) Patent No.: US 11,912,651 B2
(45) Date of Patent: Feb. 27, 2024

(54) APPARATUS AND METHOD FOR PRODUCING METHANOL

(71) Applicant: L'Air Liquide Société Anonyme pour l'Etude et l'Exploitation des Procédés Georges Claude, Paris (FR)

(72) Inventors: Karsten Covella, Frankfurt (DE); Hans Kopetsch, Bad Homburg (DE); Bryce Williams, Frankfurt am Main (DE); Julien Aoun, Frankfurt am Main (DE)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 17/692,387

(22) Filed: Mar. 11, 2022

(65) Prior Publication Data
US 2022/0289651 A1  Sep. 15, 2022

(30) Foreign Application Priority Data
Mar. 12, 2021 (EP) .................................... 21020141

(51) Int. Cl.
*C07C 29/152* (2006.01)
*B01J 19/24* (2006.01)

(52) U.S. Cl.
CPC .......... *C07C 29/152* (2013.01); *B01J 19/245* (2013.01); *B01J 19/2465* (2013.01);
(Continued)

(58) Field of Classification Search
CPC ... C07C 29/152; C07C 29/1518; C07C 31/04; C01B 2203/0255; C01B 2203/0283;
(Continued)

(56) References Cited

U.S. PATENT DOCUMENTS

2009/0018220 A1*  1/2009  Fitzpatrick .............. C12C 11/02
                                                                 518/700
2018/0354877 A1   12/2018  Sakurai

FOREIGN PATENT DOCUMENTS

| WO | WO 2006 126017 | 11/2006 |
| WO | WO 2019 005225 | 1/2019 |
| WO | WO 2020 249923 | 12/2020 |

OTHER PUBLICATIONS

Lange, Jean-Paul, Methanol synthesis: a short review of technology improvements, Catalysis Today 64 (2001), 3-8.
(Continued)

*Primary Examiner* — Jafar F Parsa
(74) *Attorney, Agent, or Firm* — Elwood L. Haynes

(57) ABSTRACT

A method and apparatus for producing methanol from a synthesis gas is provided. The method includes (i) producing, in a partial oxidation chamber, the synthesis gas having a stoichiometric number of less than 1.8 by performing a partial oxidation process with a hydrocarbon stream and an oxygen stream, (ii) passing, in a water-gas shift reactor, the synthesis gas over a water-gas shift catalyst to convert at least a portion of carbon monoxide and water into hydrogen and carbon dioxide, (iii) producing a dry, shifted synthesis gas by separating liquid condensate from shifted synthesis gas, (iv) combining, in a recycle compressor, the dry, shifted synthesis gas with a recycle synthesis gas comprised of unreacted synthesis gas and a hydrogen rich product to form a mixed synthesis gas stream, and (v) converting, in a cooled methanol synthesis reactor, at least a portion of the mixed synthesis gas stream into methanol.

11 Claims, 4 Drawing Sheets

(52) U.S. Cl.
CPC ............... *B01J 2219/00051* (2013.01); *B01J 2219/00162* (2013.01); *B01J 2219/00186* (2013.01)

(58) Field of Classification Search
CPC ...... C01B 2203/0495; C01B 2203/061; C01B 3/48; C01B 3/36
See application file for complete search history.

(56) References Cited

OTHER PUBLICATIONS

European Search Report and Written Opinion for corresponding EP 21020141, dated Aug. 6, 2021.

\* cited by examiner

PRODUCING, IN A PARTIAL OXIDATION CHAMBER, A SYNTHESIS GAS HAVING A STOICHIOMETRIC NUMBER OF LESS THAN 1.8 BY PERFORMING A PARTIAL OXIDATION PROCESS WITH A HYDROCARBON STREAM AND AN OXYGEN STREAM
302

PASSING, IN A WATER-GAS SHIFT REACTOR, THE SYNTHESIS GAS OVER A WATER-GAS SHIFT CATALYST TO CONVERT AT LEAST A PORTION OF CARBON MONOXIDE (CO) AND WATER ($H_2O$) INTO HYDROGEN (H) AND CARBON DIOXIDE ($CO_2$)
304

PRODUCING A DRY, SHIFTED SYNTHESIS GAS BY SEPARATING LIQUID CONDENSATE FROM SHIFTED SYNTHESIS GAS
306

APPARATUS AND METHOD FOR PRODUCING METHANOL

CROSS REFERENCE TO RELATED APPLICATIONS

This application claims the benefit of priority under 35 U.S.C. § 119 (a) and (b) to European Patent Application No. 21020141.4, filed Mar. 12, 2021, the entire contents of which are incorporated herein by reference.

TECHNICAL FIELD

The present disclosure relates generally to methanol production; more specifically, the present disclosure relates to an apparatus and a method for producing methanol from a synthesis gas that is generated by a non-catalytic partial oxidation (PDX).

BACKGROUND

A most commonly used process for producing methanol from a hydrocarbon gas stream is a catalytic steam reforming method. The catalytic steam reforming method may use up to three catalytic steps, wherein these steps include a pre-reforming step, a primary reforming step and a secondary reforming step; these steps are used for larger plants to produce an optimum synthesis gas for methanol production. A standard practice for producing the synthesis gas in the larger plants is to use a combined reforming method. In the combined reforming method, a first portion of a hydrocarbon gas stream is treated in a steam methane reformer (SMR) and the SMR effluent, together with a second portion of the hydrocarbon gas stream is treated in an autothermal reformer (ATR). In the above scenario, the SMR is a primary reformer and the ATR is a secondary reformer. For smaller plants, the SMR alone is used to produce the synthesis gas. However, the synthesis gas, produced through SMR alone, is an over-stoichiometric synthesis gas containing too much hydrogen.

A less common approach for producing synthesis gas is a non-catalytic partial oxidation (PDX) process. Unfortunately, the non-catalytic partial oxidation (PDX) process produces unsuitable, sub-stoichiometric synthesis gas that is deficient of hydrogen. Therefore, measures need to be applied in order to increase the hydrogen amount in the synthesis gas to a methanol synthesis loop.

In regards to methanol synthesis, a stoichiometric number (SN) may be defined to characterize the gas composition towards methanol synthesis as follows:

$$SN=\{H_2-CO_2\}/\{CO+CO_2\}$$

where $H_2$, $CO$ and $CO_2$ are mole fractions or mole percentages in the gas composition. The required SN for methanol production is 2.0. As described in the preceding paragraphs, SMR produces syngas with SN greater than about 3. Combined reforming can produce exactly 2.0 and PDX produces <2. The exact SN values for each reforming process depend on the feedstock composition as well as design and choice of operating conditions.

Some existing approaches route a portion of the sub-stoichiometric synthesis gas to a hydrogen recovery unit or a membrane to recover and reuse the hydrogen to adjust the hydrogen content of the synthesis gas. However, the above approach may result in large amounts of tail gas and poor carbon efficiency regarding the methanol production. Moreover, a practice of routing the sub-stoichiometric synthesis gas to a hydrogen recovery or membrane unit is routinely considered for ATR-only designs at extremely large scale production quantities, namely greater quantities than about 7500 metric tons per day (MTPD) methanol production, because the SMR would be infeasibly large and therefore uneconomic in an SMR-only or combined reforming setup for synthesis gas production of that scale.

Other existing approaches increase hydrogen amount by lowering the recycle ratio in the methanol synthesis loop. Thus, it generates a larger purge gas stream from which hydrogen is recovered and recycled to the make-up gas. However, this results in a low carbon efficiency and increased demand of fresh synthesis gas for the synthesis.

Other known approaches combine an amount of a hydrogen feedstock with a synthesis gas to adjust a stoichiometric balance for methanol synthesis. However, this requires a suitable hydrogen source of an appropriate size which can be detrimental for the production economics. For example, hydrogen produced by electrolysis could be used for this purpose; however, its production is still relatively expensive and it is not always available at a site of methanol production plants. Alternatively, import hydrogen supply from any external sources may simply be unavailable at a location of the methanol production plants.

Typically, methanol production processes utilize a combination of different catalytic reforming steps to avoid hydrogen deficiency in the synthesis gas. However, the catalytic reforming method requires significant capital expenditure which is especially not favorable for smaller plants where capital and engineering costs weigh more heavily onto cost of the methanol production. A secondary key problem for the smaller plants is that each equipment item adds considerable contribution to a total investment cost and production cost due to the required engineering effort.

It is also common to use a water-gas-shift reactor to convert carbon monoxide (CO) and water ($H_2O$) into hydrogen ($H_2$) and carbon dioxide ($CO_2$). In conventional apparatus, use of water-gas-shift reactor results in a need for additional steps such as pressure-swing absorption (PSA), membrane filtering, amine wash, physical absorption to separate $CO_2$ from the synthesis gas to increase SN in the synthesis gas.

Although several approaches are presently available to compensate hydrogen deficiency, they result in a higher investment cost, especially, for smaller plants. Such an increase in the investment cost is not affordable in many situations.

Therefore, there arises a need to address the aforementioned technical drawbacks in existing technologies in producing methanol from the sub-stoichiometric synthesis gas.

SUMMARY

The present disclosure seeks to provide an improved approach to produce methanol from a synthesis gas that is generated by a non-catalytic partial oxidation (PDX) with simplified apparatus, low investment cost and low production cost. An aim of the present disclosure is to provide a solution that overcomes at least partially problems encountered in prior art and provide an improved method and an improved apparatus for producing methanol from the synthesis gas that is generated by the non-catalytic partial oxidation (PDX), which do not require use of a complicated multi-tube steam reformer. The object of the present disclosure is achieved by solutions defined in the enclosed independent claims. Advantageous implementations of the present disclosure are further defined in the dependent claims.

According to a first aspect, there is provided a method for producing methanol from a synthesis gas, characterized in that the method comprises:

producing, in a partial oxidation (PDX) chamber, the synthesis gas having a stoichiometric number of less than substantially 1.8 by performing a partial oxidation (PDX) process with a hydrocarbon stream and an oxygen stream;

passing, in a water-gas shift reactor, the synthesis gas over a water-gas shift catalyst to convert at least a portion of carbon monoxide (CO) and water ($H_2O$) into hydrogen ($H_2$) and carbon dioxide ($CO_2$) thus obtaining a shifted synthesis gas;

producing a dry, shifted synthesis gas by separating liquid condensate from the shifted synthesis gas;

combining, in a recycle compressor, the dry, shifted synthesis gas with a recycle synthesis gas comprising unreacted synthesis gas and a hydrogen rich product to form a mixed synthesis gas stream; and converting, in a cooled methanol synthesis reactor, at least a portion of the mixed synthesis gas stream into methanol.

The improved method for producing methanol is of advantage in that the method uses a partial oxidation (PDX) process as a single source for the synthesis gas production. Moreover, the method may use a single recycle compressor within a methanol synthesis loop and a common steam drum for collecting steam generated by water-cooling of the water-gas shift reactor and the cooled methanol synthesis reactor, so that a number of equipment are significantly reduced which in turn reduces the investment cost. Furthermore, the heat of reaction in the water-gas shift reactor and in the cooled methanol synthesis reactor may be utilized for the steam production which in turn reduces the production cost. Thus, the improved method according to the present disclosure is especially favorable for smaller plants or modular plants still providing suitable synthesis gas mixture for methanol production.

The method increases the hydrogen ($H_2$) content during a water-gas shift reaction by converting the portion of the carbon monoxide (CO) and the water ($H_2O$) in the synthesis gas into the hydrogen ($H_2$) and the carbon dioxide ($CO_2$), thus leading to favorable stoichiometry and preventing hotspots that might otherwise occur in the cooled methanol synthesis reactor at high carbon monoxide (CO) contents.

According to a second aspect, there is provided an apparatus for producing methanol from a synthesis gas, characterized in that the apparatus comprises, in a series:

a partial oxidation (PDX) chamber for producing the synthesis gas having a stoichiometric number of less than substantially 1.8 by performing a partial oxidation (PDX) process with a hydrocarbon stream and an oxygen stream;

a water-gas shift reactor for passing the synthesis gas over a water-gas shift catalyst to convert at least a portion of carbon monoxide (CO) and water ($H_2O$) into hydrogen ($H_2$) and carbon dioxide ($CO_2$) thus obtaining a shifted synthesis gas;

a condensate separator for separating liquid condensate from the shifted synthesis gas to produce a dry, shifted synthesis gas;

a recycle compressor for combining the dry, shifted synthesis gas with a recycle synthesis gas comprising unreacted synthesis gas and a hydrogen rich product to form a mixed synthesis gas stream; and a cooled methanol synthesis reactor for converting at least a portion of the mixed synthesis gas stream into methanol.

The apparatus for producing methanol is of advantage in that the apparatus uses a partial oxidation (PDX) process as a single source for the synthesis gas production. Moreover, the apparatus includes a single recycle compressor within a methanol synthesis loop and a common steam drum for collecting steam generated by water-cooling of the water-gas shift reactor and the cooled methanol synthesis reactor by boiling water, so that a number of equipment required is significantly reduced which in turn reduces the investment cost. Furthermore, the heat of reaction in the water-gas shift reactor and the cooled methanol synthesis reactor may be utilized for the steam production which in turn reduces the production cost. Thus, the apparatus according to the present disclosure is especially favorable for smaller plants or modular plants still providing suitable synthesis gas mixture for methanol production.

The water-gas shift reactor increases the hydrogen ($H_2$) content during a water-gas shift reaction by converting the portion of the carbon monoxide (CO) and the water ($H_2O$) in the synthesis gas into the hydrogen ($H_2$) and the carbon dioxide ($CO_2$), thus leading to favorable stoichiometry and preventing hotspots that might otherwise occur in the cooled methanol synthesis reactor at high carbon monoxide contents.

Embodiments of the present disclosure eliminate the aforementioned drawbacks in existing known approaches in producing methanol from the synthesis gas that is produced from the non-catalytic partial oxidation (PDX). The advantage of the embodiments according to the present disclosure is that the embodiments enable use of water-gas shift reactor downstream of the partial oxidation (PDX) chamber and upstream of the cooled methanol synthesis reactor in combination with a hydrogen purification of the purge gas from lower recycle ratio operation to adjust stoichiometry and the hydrogen content of the synthesis gas for methanol production. The present embodiments are cost effective because they do not require complex apparatus set ups and do not result in a requirement for additional steps for compensating hydrogen deficiency of the sub-stoichiometric synthesis gas.

Additional aspects, advantages, features and objects of the present disclosure are made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those familiar with the art will understand that the drawings are not to scale. Wherever possible, like elements have been indicated by identical numbers.

Embodiments of the present disclosure will now be described, by way of example only, with reference to the following diagrams wherein:

FIG. 3A is a flowchart illustrating steps of a method for producing methanol from a synthesis gas, in accordance with an embodiment of the present disclosure.

Figure 1:
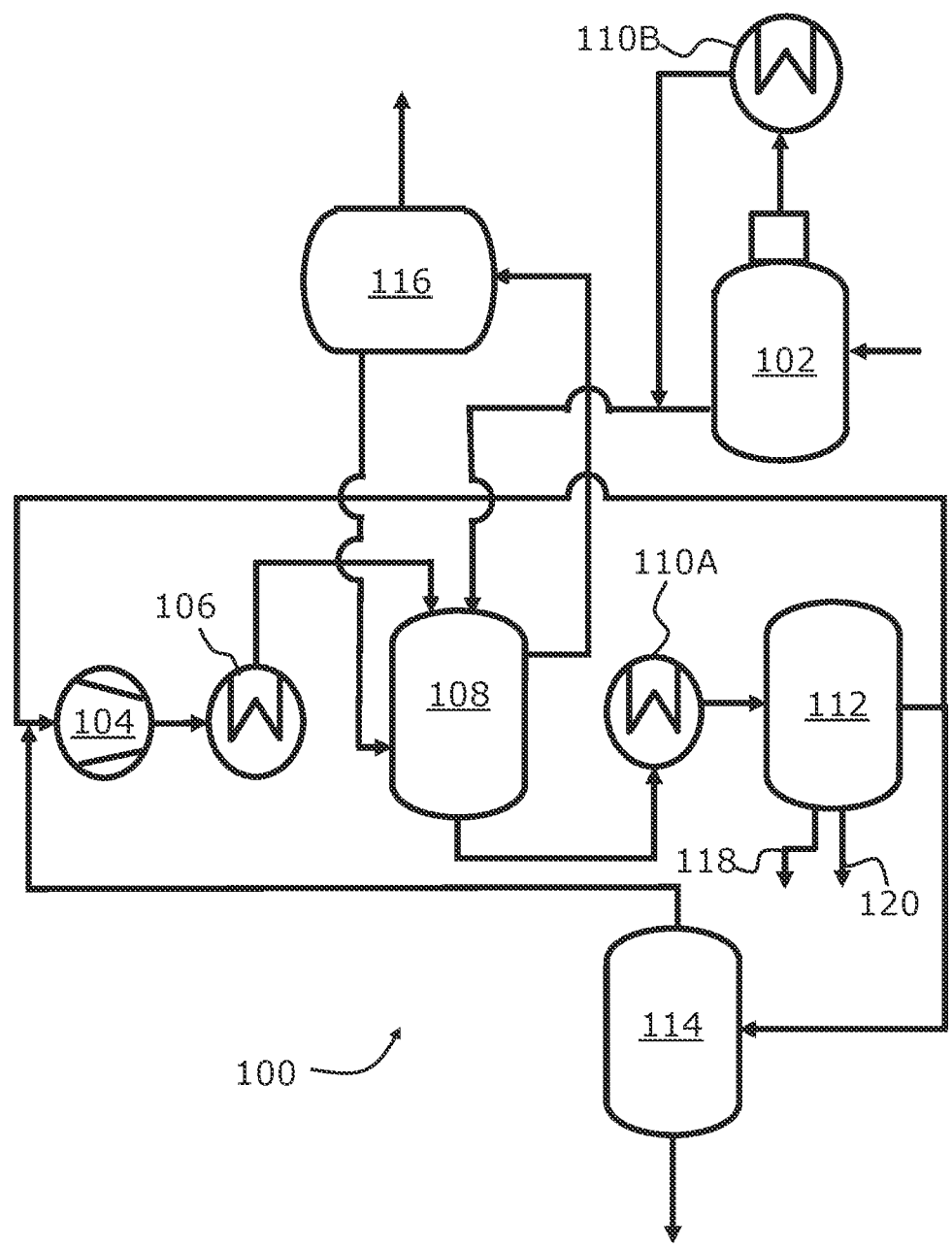
FIG. 1 is a schematic illustration of a first implementation of an apparatus for producing methanol from a synthesis gas, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF PREFERRED EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

According to a first aspect, there is provided a method for producing methanol from a synthesis gas, characterized in that the method comprises:
- producing, in a partial oxidation (PDX) chamber, the synthesis gas having a stoichiometric number of less than substantially 18 by performing a partial oxidation (PDX) process with a hydrocarbon stream and an oxygen stream;
- passing, in a water-gas shift reactor, the synthesis gas over a water-gas shift catalyst to convert at least a portion of carbon monoxide (CO) and water ($H_2O$) into hydrogen ($H_2$) and carbon dioxide ($CO_2$) for obtaining a shifted synthesis gas;
- producing a dry, shifted synthesis gas by separating liquid condensate from the shifted synthesis gas;
- combining, in a recycle compressor, the dry, shifted synthesis gas with a recycle synthesis gas comprising unreacted synthesis gas and a hydrogen rich product to form a mixed synthesis gas stream; and
- converting, in a cooled methanol synthesis reactor, at least a portion of the mixed synthesis gas stream into methanol.

The method for producing methanol is of advantage in that the method uses a partial oxidation (PDX) process as a single source for the synthesis gas production. Moreover, the method may use a single recycle compressor within a methanol synthesis loop and a common steam drum for collecting steam generated by water-cooling of the water-gas shift reactor and the cooled methanol synthesis reactor so that the number of equipment is significantly reduced which in turn reduces the investment cost. Furthermore, the heat of reaction in the water-gas shift reactor and the cooled methanol synthesis reactor may be utilized for steam production which in turn reduces the production cost. Thus, the method according to the present disclosure is especially favorable for smaller plants or modular plants still providing suitable synthesis gas mixture for methanol production.

According to an embodiment, the hydrocarbon stream is a natural gas, coal gas, methane hydrates, and/or comprises hydrocarbons like naphtha or other hydrocarbons which are liquid under ambient conditions, e. g. refinery residues, cracker residues or the like.

The partial oxidation process (PDX) is a non-catalytic, exothermic reaction where the hydrocarbon stream and the oxygen stream react to produce the synthesis gas. The partial oxidation process (PDX) may be performed in the presence of steam and/or carbon dioxide as a moderator.

Optionally, the method comprises cooling the synthesis gas to a first temperature without condensation of water vapor occurring, before passing the synthesis gas over the water-gas shift catalyst, thus simplifying an apparatus set up for methanol production and reduces the investment cost. The first temperature may be in a range of 200° C. to 300° C.

According to an embodiment, the water-gas shift catalyst includes a low-temperature water-gas shift catalyst, a high temperature water-gas shift catalyst, or an isothermal and medium temperature water-gas shift catalyst (for example, functioning in a temperature range of 220° C. to 320° C.). According to an embodiment, the heat of reaction in the water-gas shift reactor is managed by circulating water, either natural or pumped, to produce steam.

Optionally, in the method, producing the dry, shifted synthesis gas comprises:
- cooling, in a first cooling unit, the shifted synthesis gas to a point of condensation at a second temperature (for example, in a range of 50° C. to 150° C.) to form the liquid condensate; and
- separating, in a condensate separator, the liquid condensate from the shifted synthesis gas to produce the dry, shifted synthesis gas.

Optionally, the method comprises:
- cooling, in a second cooling unit, an effluent from the cooled methanol synthesis reactor to a point of condensation at a third temperature (for example, in a range of typically 40° C. to 60° C.) to produce a condensate that comprises crude methanol and water; and
- separating, in a methanol separator, the crude methanol from unreacted synthesis gas.

The method also comprises:
- routing a first portion of the unreacted synthesis gas from the methanol separator as the recycle synthesis gas to the recycle compressor;
- routing a second portion of the unreacted synthesis gas from the methanol separator, to a hydrogen recovery unit, for example PSA; and
- producing, in the hydrogen recovery unit, the hydrogen rich product to be mixed with the recycle synthesis gas stream to the recycle compressor to form the mixed synthesis gas stream.

The hydrogen recovery unit may be a pressure-swing absorption (PSA) hydrogen recovery unit.

According to an embodiment, the method includes lowering a recycle ratio in the methanol synthesis loop and generating thus a purge gas stream from which the hydrogen content is recovered and recycled to the mixed synthesis gas stream.

Optionally, the method comprises compressing, in the recycle compressor, the mixed synthesis gas stream by increasing the pressure of the mixed synthesis gas stream.

Optionally, the method comprises
mixing both the hydrocarbon stream and the oxygen stream with steam up to about 30% in volume in each flow; and/or
preheating the hydrocarbon stream and the oxygen stream before supplying to the partial oxidation (PDX) chamber for performing the partial oxidation (PDX) process.

Optionally, in the method, (i) cooling of the shifted synthesis gas to the point of condensation and separating the liquid condensate from the shifted synthesis gas and (ii) cooling methanol synthesis reactant effluent to the point of condensation and separating the crude methanol from unreacted synthesis gas, are performed in an equipment that is common to (i) and (ii).

Optionally, the method includes arranging for the water-gas shift reactor and the cooled methanol synthesis reactor to share a common coolant and steam generation system, for example a common steam generating system in case both reactors are cooled by boiling water. The method advantageously reduces a significant number of equipment required for methanol production, thus reducing the investment cost.

Optionally, the method includes containing the water-gas shift reactor and the cooled methanol synthesis reactor in the same vessel. The method advantageously reduces a significant number of equipment required for methanol production, thus reducing the investment cost.

Optionally, the method comprises operating the partial oxidation (PDX) chamber and the water-gas shift reactor under a pressure condition in a range of 30 to 90 bar.

According to an embodiment, the partial oxidation (PDX) process is performed under a pressure condition nominally that is greater than about 30 bar. The partial oxidation (PDX) process may be performed under a pressure condition that is beneficially more than about 60 bar. The partial oxidation (PDX) process may be performed under a pressure condition that is most beneficially between 60 to 90 bar.

According to an embodiment, the passing (namely, shifting) of synthesis gas is performed under a pressure condition that is nominally greater than about 30 bar. The shifting of synthesis gas may be performed under a pressure condition that is beneficially more than about 60 bar. The shifting of synthesis gas may be performed under a pressure condition that is most beneficially between 60 to 90 bar.

According to a second aspect, there is provided an apparatus for producing methanol from a synthesis gas, characterized in that the apparatus comprises, in a series:
a partial oxidation (PDX) chamber for producing the synthesis gas having a stoichiometric number of less than substantially 1.8 (for example, 1.83) by performing a partial oxidation (PDX) process with a, preferably preheated, hydrocarbon stream and an, preferably preheated, oxygen stream;
a water-gas shift reactor for passing (namely, shifting) the synthesis gas over a water-gas shift catalyst to convert at least a portion of carbon monoxide (CO) and water ($H_2O$) into hydrogen ($H_2$) and carbon dioxide ($CO_2$) for obtaining a shifted synthesis gas;
a condensate separator for separating liquid condensate from shifted synthesis gas to produce a dry, shifted synthesis gas;
a recycle compressor for combining the dry, shifted synthesis gas with a recycle synthesis gas comprised of unreacted synthesis gas and a hydrogen rich product to form a mixed synthesis gas stream; and
a cooled methanol synthesis reactor for converting at least a portion of the mixed synthesis gas stream into methanol.

The apparatus for producing methanol is of advantage in that the apparatus uses a partial oxidation (PDX) process as a single source for the synthesis gas production. Moreover, the apparatus includes a single recycle compressor within a methanol synthesis loop and a common steam drum for collecting steam generated by cooling the water-gas shift reactor and the cooled methanol synthesis reactor with boiling water so that a number of equipment required is significantly reduced which in turn reduces the investment cost. Furthermore, the heat of reaction in the water-gas shift reactor and the cooled methanol synthesis reactor may be utilized for steam production which in turn reduces the production cost. Thus, the apparatus according to the present disclosure is especially favorable for smaller plants or modular plants still providing suitable synthesis gas mixture for methanol production.

According to an embodiment, the hydrocarbon stream is a natural gas, coal gas, or methane hydrates, and/or comprises hydrocarbons like naphtha or other hydrocarbons which are liquid under ambient conditions, e. g. refinery residues, cracker residues or the like.

The partial oxidation process (PDX) is a non-catalytic, exothermic reaction where the hydrocarbon stream and the oxygen stream react to produce the synthesis gas. The partial oxidation (PDX) process may be performed in the presence of steam and/or carbon dioxide as a moderator.

A cooling apparatus, such as a waste heat boiler, may be used to cool the synthesis gas to a first temperature without condensation of water vapor occurring before passing the synthesis gas over the water-gas shift catalyst. The first temperature may be in a range of 200° C. to 300° C.

The apparatus advantageously routes the synthesis gas from the partial oxidation (PDX) chamber to the water-gas shift reactor without cooling below the dew point and subsequently cooling the synthesis gas in the water-gas shift reactor, thus simplifying the apparatus set up for methanol production and reduces its investment cost.

According to an embodiment, the water-gas shift catalyst includes a low-temperature water-gas shift catalyst, a high temperature water-gas shift catalyst, an isothermal and medium temperature water-gas shift catalyst (for example, functioning in a range of 220° C. to 320° C.).

According to an embodiment, the heat of reaction in the water-gas shift reactor is managed by circulating water, either natural or pumped, to produce steam.

Optionally, the apparatus comprises:
a first cooling unit for cooling the shifted synthesis gas to a point of condensation at a second temperature (for example, in a range of 50° C. to 150° C.) to form the liquid condensate.

Optionally, the apparatus comprises:
a second cooling unit for cooling an effluent from the cooled methanol synthesis reactor to a point of condensation at a third temperature (for example, in a range of 40° C. to 60° C.) to produce a condensate that comprises crude methanol and water; and
a methanol separator for separating the crude methanol from unreacted synthesis gas.

In the apparatus, the methanol separator is configured to route a first portion of the unreacted synthesis gas as the recycle synthesis gas to the recycle compressor.

The apparatus comprises
a hydrogen recovery unit, such as a pressure-swing absorption (PSA), for (i) receiving a second portion of the unreacted synthesis gas, from the methanol separator, and (ii) producing the hydrogen-rich product to be mixed with the recycle synthesis gas stream to the recycle compressor to form the mixed synthesis gas stream.

According to an embodiment, the apparatus lowers a recycle ratio in the methanol synthesis loop and generates thereby a purge gas stream from which the hydrogen content is recovered and recycled to the mixed synthesis gas stream.

Optionally, the apparatus is configured to mix both the hydrocarbon stream and the oxygen stream with steam and/or preheat the hydrocarbon stream and the oxygen stream before supplying to the partial oxidation (PDX) chamber for performing the partial oxidation (PDX) process.

Optionally, in the apparatus, the recycle compressor is configured to compress the mixed synthesis gas stream by increasing the pressure of the mixed synthesis gas stream.

Optionally, the apparatus comprises:
a steam drum for providing steam generated by cooling the water-gas shift reactor and the cooled methanol synthesis reactor with boiling water.

Optionally, in the apparatus, the water-gas shift reactor and the cooled methanol synthesis reactor share a common coolant and steam generation system, thus reducing an investment cost involved.

Optionally, in the apparatus, the water-gas shift reactor and the cooled methanol synthesis reactor are contained together in the same vessel.

Optionally, in the apparatus, the partial oxidation (PDX) chamber and the water-gas shift reactor are configured to operate under a pressure condition that is in the range of 30 to 90 bar.

According to an embodiment, the partial oxidation (PDX) process is performed under a pressure condition nominally greater than about 30 bar. The partial oxidation (PDX) process may be performed under a pressure condition beneficially more than about 60 bar. The partial oxidation (PDX) process may be performed under a pressure condition most beneficially between 60 to 90 bar.

According to an embodiment, the passing (namely, shifting) of synthesis gas is performed under pressure condition nominally greater than about 30 bar. The shifting of synthesis gas may be performed under a pressure condition beneficially more than about 60 bar. The shifting of synthesis gas may be performed under a pressure condition most beneficially between 60 to 90 bar.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

FIG. 1 is a schematic illustration of a first implementation of an apparatus 100 for producing methanol from a synthesis gas, in accordance with an embodiment of the present disclosure. The apparatus 100 includes a partial oxidation (PDX) chamber 102, a recycle compressor 104, a heating unit 106, a water-gas shift methanol reactor 108, a cooling unit 110A, a vapor-liquid separator 112, a hydrogen recovery unit 114, and a steam drum 116, The apparatus 100 further includes a second cooling unit 110B. The partial oxidation (PDX) chamber 102 is configured to receive a hydrocarbon stream and a oxygen stream and produce the synthesis gas having a stoichiometric number of less than 1.8 by performing a partial oxidation (PDX) process with the hydrocarbon stream and the oxygen stream. The hydrocarbon stream and oxygen stream are preheated to a first temperature; the first temperature is beneficially in a temperature range of 150° C. to 500° C. The hydrocarbon stream and oxygen stream are optionally mixed with steam from the steam drum 116 or other sources.

The water-gas shift/methanol reactor 108 in the first implementation is designed to maintain separate the reaction of recycle syngas to methanol from the water-gas shift (WGS) reaction of cooled PDX gas. The second cooling unit 110B is connected to downstream of the partial oxidation (PDX) chamber 102 and is configured to cool an effluent of the partial oxidation (PDX) process to form cooled synthesis gas. A shift portion of the water-gas shift/methanol reactor 108 is configured to receive the cooled synthesis gas from the second cooling unit 110B, with contained water vapor. The shift portion of the water-gas shift/methanol reactor 108 may convert at least a portion of carbon monoxide (CO) and water ($H_2O$) in the synthesis gas into hydrogen ($H_2$) and carbon dioxide ($CO_2$). The methanol synthesis portion of the water-gas shift/methanol reactor 108 is configured to receive the heated, dry and unreacted recycle synthesis gas from the recycle gas compressor 104 and the heating unit 106. The methanol synthesis portion of the water-gas shift/methanol reactor 108 may convert at least a portion of the carbon monoxide (CO) and hydrogen ($H_2$) to methanol.

The water-gas shift/methanol reactor 108 may be a cooled reactor and operates preferably in a pressure range of 60 to 90 bar. The heat of reaction in the water-gas shift/methanol reactor 108 is managed by circulating water, either naturally circulating or pumped, to produce the steam. The steam or water vapor is separated from the circulated water in the steam drum 116. After separation of the steam from the circulated water, the water is available for recirculation to produce additional steam.

As shown, the cooling unit 110A is configured to cool the effluent from reactor 108; optionally, it can be configured to receive two separate effluents from the water-gas shift/methanol reactor 108 (namely, from the shift portion and methanol synthesis portion of the water-gas shift/methanol reactor 108) and form a combined condensate by cooling the effluents to a second temperature or to form two separate condensates (namely, first condensate and second condensate) by cooling the effluents to the second temperature; the second temperature is beneficially in a range of 40 to 80° C. The second temperature may be 40° C., 45° C., 50° C., 55° C., 60° C., 65° C., 70° C., 75° C. or 80° C. Cooling may be achieved by interchange with cold process streams or with cooling utilities or a combination thereof. The cooling utilities may include air or cooling water. A first portion of the cooling of the effluents may be performed by heat exchange with a feed to the water-gas shift/methanol reactor 108. A second portion of the cooling of the effluents may be performed by using the cooling utilities, to form the first condensate. The vapor-liquid separator 112 is configured to receive the first condensate from the cooling unit 110A and form a dry, unreacted synthesis gas as a make-up gas for methanol production, by removing liquid condensate.

The vapor-liquid separator 112 can optionally be configured to accept two separate effluent streams from the cooling unit 110A or a single, combined effluent from the cooling unit 110A. Downstream of the vapor-liquid separator 112, the crude methanol is collected via a second stream line 120 and optionally a condensate is collected via a first stream line 118. The vapor-liquid separator 112 is configured to collect the crude methanol for subsequent purification, which is not shown in FIG. 1. The crude methanol may be optionally collected separately or together with the condensate from the water-gas shift/methanol reactor effluent. Effluents from the water-gas shift/methanol reactor 108 may be maintained as separate up to the vapor-liquid separator 112. A baffle in the methanol separator 112 may separate water-gas shift/methanol reactor condensate.

A vapor phase from the vapor-liquid separator 112 is split into a first portion that is recycled directly and a second portion that is purged from the methanol synthesis loop to the hydrogen recovery unit 114. The hydrogen recovery unit 114 may be a pressure swing absorption (PSA) hydrogen recovery unit. The hydrogen recovery unit 114 produces hydrogen-rich product that is recombined with a recycle gas and returned to the suction of the recycle compressor 104. Remaining gas, a tail gas, from the pressure-swing absorption (PSA) hydrogen recovery unit 114 is purged for use as a fuel.

The recycle compressor 104 may increase the pressure of the synthesis gas to overcome a pressure drop in the methanol synthesis loop. Typical pressures are above about 60 bar and up to about 90 bar, namely corresponding approximately to the PDX pressure. The temperature of the pressurized synthesis gas mixture is increased in the heating unit 106. Typical temperatures begin to approach methanol synthesis temperatures of 220° C. to 300° C. Heating may be implemented by interchange with hot process streams, with heating utilities or a combination thereof. The heating unit 106 and the cooling unit 110A are coupled at cold and hot sides, respectively, of a process gas interchanger. Preheated synthesis gas mixture is fed to the water-gas shift/methanol reactor 108. Heat released from water-gas shift reaction and methanol synthesis is managed collectively in a single reactor and a single steam drum 116.

Figure 2:
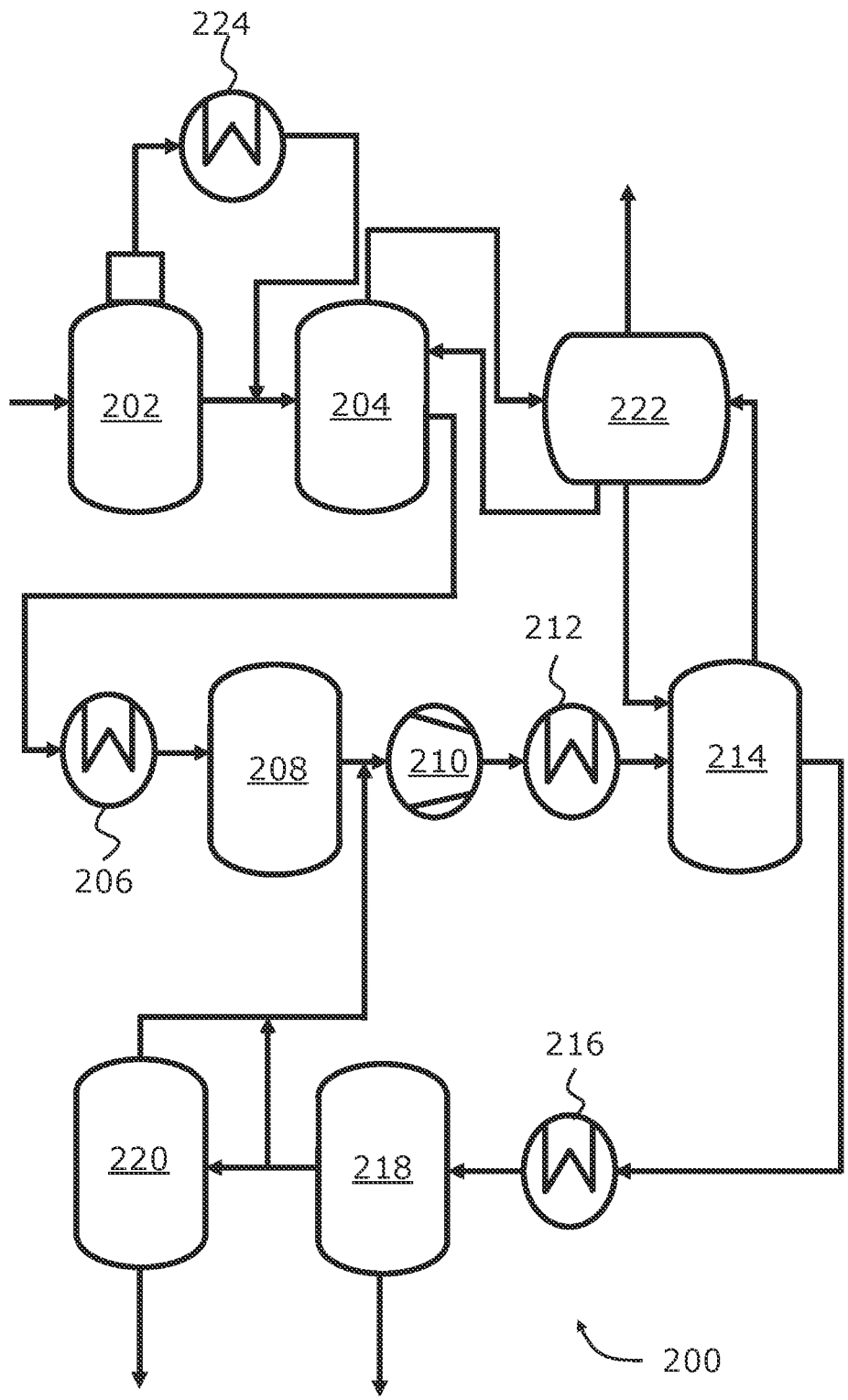
FIG. 2 is a schematic illustration of a second implementation of an apparatus for producing methanol from a synthesis gas, in accordance with an embodiment of the present disclosure.

FIG. 2 is a schematic illustration of a second implementation of an apparatus 200 for producing methanol from a synthesis gas, in accordance with an embodiment of the present disclosure. The apparatus 200 includes, in a series, a partial oxidation (PDX) chamber 202, a cooling device 224, a water-gas shift reactor 204, a first cooling unit 206, a condensate separator 208, a recycle compressor 210, a heating unit 212, a cooled methanol synthesis reactor 214, a second cooling unit 216, a methanol separator 218, a hydrogen recovery unit 220 and a steam drum 222. The partial oxidation (PDX) chamber 202 is configured to receive a hydrocarbon stream and an oxygen stream and produce the synthesis gas having a stoichiometric number of less than 1.8 by performing a partial oxidation (PDX) process with the hydrocarbon stream and the oxygen stream. The cooling device 224 is configured to cool partial oxidation (PDX) effluent such as the synthesis gas, optionally without condensation. The cooling device 224 partially cools the synthesis gas. The water-gas shift reactor 204 is configured to receive partially cooled synthesis gas and passing the synthesis gas over a water-gas shift catalyst to convert at least a portion of carbon monoxide (CO) and water ($H_2O$) into hydrogen ($H_2$) and carbon dioxide ($CO_2$) for obtaining a shifted synthesis gas. The water-gas shift reactor 204 is cooled at a first temperature typically in a range of 200° C. to 300° C. by boiling water to remove the heat of reaction. The first cooling unit 206 is configured to receive the shifted synthesis gas and cool the shifted synthesis gas to the point of condensation at a second temperature typically 40° C. to 80° C. to form a liquid condensate. Cooling may be implemented by interchange with cold process streams, with cooling utilities or a combination thereof. The condensate separator 208 is configured to receive the cooled shifted synthesis gas and produce a dry, shifted synthesis gas by separating the liquid condensate from the cooled shifted synthesis gas (not shown). The recycle compressor 210 is configured to receive a mixed syngas which is the combination of the dry, shifted synthesis gas and a recycle synthesis gas comprising unreacted synthesis gas and a hydrogen rich product. The recycle compressor 210 may increase the synthesis gas pressure to overcome pressure drop in a methanol synthesis loop. The heating unit 212 is configured to receive the mixed synthesis gas stream and heat the mixed synthesis gas stream to methanol conversion temperatures in a range of 200° C. to 300° C. Heating may be implemented by interchange with hot process streams or with heating utilities or a combination thereof.

The cooled methanol synthesis reactor 214 is configured to receive the preheated mixed synthesis gas stream and convert at least a portion of the mixed synthesis gas stream into methanol. The second cooling unit 216 is configured to receive an effluent from the cooled methanol synthesis reactor 214 and cool the effluent to a point of condensation at a third temperature, typically 40° C. to 80° C., to produce a condensate that includes crude methanol and water. A first portion of the cooling of the effluent may be performed by heat exchange with a feed to the cooled methanol synthesis reactor 214. A second portion of the cooling of the effluent may be performed by using the cooling utilities, to form the condensate that includes crude methanol and water. The heating unit 212 and the second cooling unit 216 are cold and hot sides, respectively, of a process gas interchanger. The methanol separator 218 is configured to receive the gas-liquid mixture from the second cooling unit 216 and separate the crude methanol from unreacted synthesis gas. A first portion of the unreacted synthesis gas is provided directly as the recycle synthesis gas to the recycle compressor 210. A second portion of the unreacted synthesis gas, from the methanol separator 218, is fed to the hydrogen recovery unit 220 for producing the hydrogen rich product to be mixed with the recycle synthesis gas stream to the recycle compressor 210 to form the mixed synthesis gas stream. The hydrogen recovery unit 220 may be a pressure swing absorption (PSA) hydrogen recovery unit.

Heat of the reaction in the water-gas shift reactor 204 and the cooled methanol synthesis reactor 214 is managed by circulating water, either naturally circulating or pumped, to produce steam. The steam in the circulated water is separated in the steam drum 222. After separation of the steam in the circulated water, the water is available for recirculation.

Figure 3B:
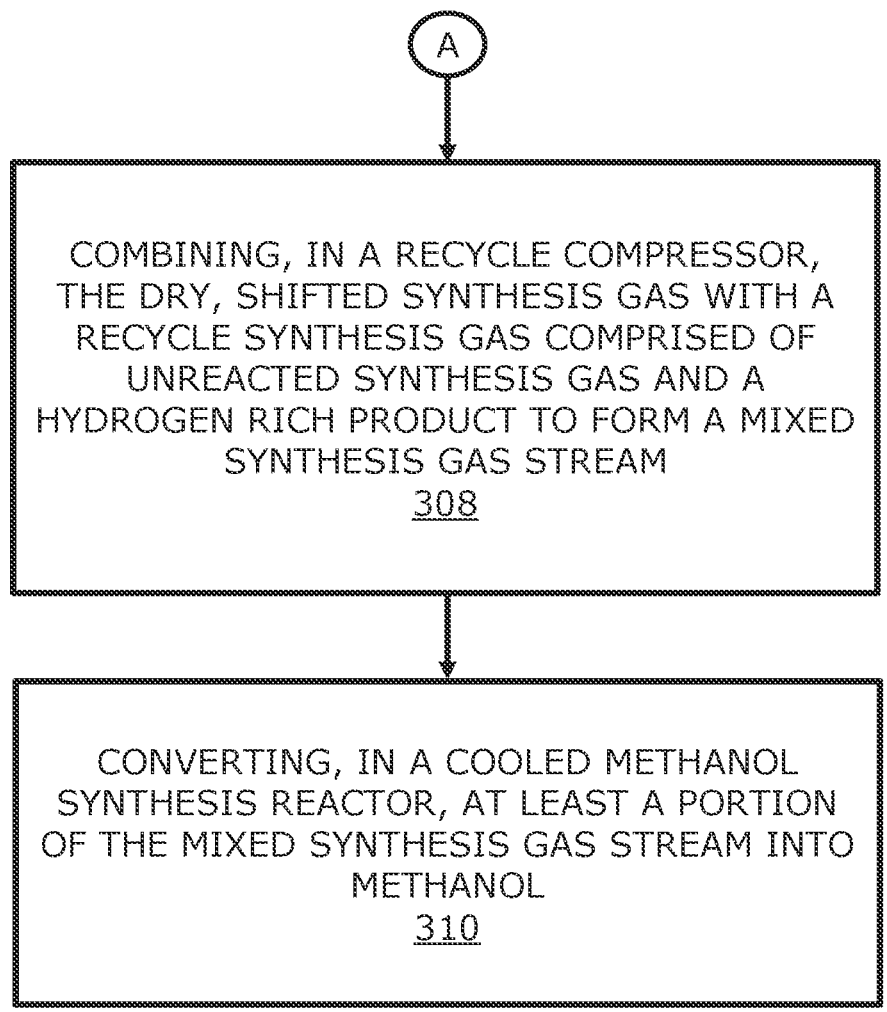
FIG. 3B is a flowchart illustrating steps of a method for producing methanol from a synthesis gas, in accordance with an embodiment of the present disclosure.

FIGS. 3A and 3B are flowcharts illustrating steps of a method for producing methanol from a synthesis gas, in accordance with an embodiment of the present disclosure. At a step 302, the synthesis gas having a stoichiometric number of less than 1.8 is produced in a partial oxidation (PDX) chamber by performing a partial oxidation (PDX) process with a hydrocarbon stream and an oxygen stream. At a step 304, the synthesis gas is passed over a water-gas shift catalyst to convert at least a portion of carbon monoxide (CO) and water ($H_2O$) into hydrogen ($H_2$) and carbon dioxide ($CO_2$) for obtaining a shifted synthesis gas. At a step 306, a dry, shifted synthesis gas is produced by separating liquid condensate from the shifted synthesis gas. At a step 308, the dry, shifted synthesis gas is combined with a recycle synthesis gas comprised of unreacted synthesis gas and a hydrogen rich product to form a mixed synthesis gas stream.

At a step 310, at least a portion of the mixed synthesis gas stream is converted into methanol in a cooled methanol synthesis reactor.

Modifications to embodiments of the present disclosure described in the foregoing are possible without departing from the scope of the present disclosure as defined by the accompanying claims. Expressions such as "including", "comprising", "incorporating", "have, is" used to describe and claim the present disclosure are intended to be construed in a non-exclusive manner, namely allowing for items, components or elements not explicitly described also to be present. Reference to the singular is also to be construed to relate to the plural.

LIST OF REFERENCE NUMERALS

100, 200 apparatus
102, 202 partial oxidation (PDX) chamber
104, 210 recycle compressor
106, 212 heating unit
108 water-gas shift/methanol reactor
110A, 110B cooling unit
112 vapor-liquid separator
114, 220 hydrogen recovery unit
116, 222 steam drum
118 first stream line
120 second stream line
224 cooling device
204 water-gas shift reactor
206 first cooling unit
208 condensate separator
214 cooled methanol synthesis reactor
216 second cooling unit
218 methanol separator It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for producing methanol from a synthesis gas, comprising:
    producing, in a partial oxidation chamber, the synthesis gas having a stoichiometric number of less than 1.8 by performing a partial oxidation process with a hydrocarbon stream and an oxygen stream;
    passing, in a water-gas shift reactor, the synthesis gas over a water-gas shift catalyst to convert at least a portion of carbon monoxide and water into hydrogen and carbon dioxide thereby obtaining a shifted synthesis gas;
    producing a dry, shifted synthesis gas by separating liquid condensate from the shifted synthesis gas;
    combining, in a recycle compressor, the dry, shifted synthesis gas with a recycle synthesis gas comprised of unreacted synthesis gas and a hydrogen rich product to form a mixed synthesis gas stream; and
    converting, in a cooled methanol synthesis reactor, at least a portion of the mixed synthesis gas stream into methanol.

2. The method of claim 1, further comprising cooling the synthesis gas to a first temperature without condensation of water vapor occurring, before passing the synthesis gas over the water-gas shift catalyst.

3. The method of claim 1, wherein producing the dry, shifted synthesis gas comprises
    cooling, in a first cooling unit, the shifted synthesis gas to a point of condensation at a second temperature to form a liquid condensate; and
    separating, in a condensate separator, the liquid condensate from the shifted synthesis gas to produce the dry, shifted synthesis gas.

4. The method of claim 1, wherein the method comprises
    cooling, in a second cooling unit, an effluent from the cooled methanol synthesis reactor to a point of condensation at a third temperature to produce a condensate that comprises crude methanol and water; and
    separating, in a methanol separator, the crude methanol from unreacted synthesis gas.

5. The method of claim 4, wherein the method comprises
    routing a first portion of the unreacted synthesis gas from the methanol separator as the recycle synthesis gas to the recycle compressor;
    routing a second portion of the unreacted synthesis gas from the methanol separator, to a hydrogen recovery unit; and
    producing, in the hydrogen recovery unit, the hydrogen rich product to be mixed with the recycle synthesis gas stream to the recycle compressor to form a mixed synthesis gas stream.

6. The method of claim 1, wherein the method comprises compressing, in the recycle compressor, the mixed synthesis gas stream by increasing the pressure of the mixed synthesis gas stream.

7. The method of claim 1, wherein the method comprises
    mixing both the hydrocarbon stream and the oxygen stream with steam; and/or
    preheating the hydrocarbon stream and/or the oxygen stream before supplying to the partial oxidation chamber for performing the partial oxidation process.

8. The method of claim 1, wherein:
    (I cooling of the shifted synthesis gas to a point of condensation and separating the liquid condensate from the shifted synthesis gas; and
    (ii) cooling methanol synthesis reactant effluent to a point of condensation and separating the crude methanol from unreacted synthesis gas, are performed in an equipment that is common to (i) and (ii).

9. The method of claim 1, wherein the water-gas shift reactor and the cooled methanol synthesis reactor share a mutually common coolant and steam generation system.

10. The method of claim 1, wherein the water-gas shift reactor and the cooled methanol synthesis reactor are mutually contained in the same vessel.

11. The method of claim 1, wherein the method comprises operating the partial oxidation chamber and the water-gas shift reactor under a pressure condition in a range of 30 to 90 bar.

* * * * *